(12) United States Patent
Huitema et al.

(10) Patent No.: US 6,508,786 B2
(45) Date of Patent: Jan. 21, 2003

(54) NEEDLE POSITION LOCK

(75) Inventors: Thomas W. Huitema, Cincinnati, OH (US); Scott Nielsen Barton, Loveland, OH (US); Kip Rupp, New Richmond, OH (US); David H. Ruder, Taylorsville, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 29 days.

(21) Appl. No.: 09/863,113

(22) Filed: May 22, 2001

(65) Prior Publication Data

US 2002/0177807 A1 Nov. 28, 2002

(51) Int. Cl.[7] .......................... A61M 5/00; A61M 5/32; A61M 5/178
(52) U.S. Cl. .................. 604/116; 604/117; 604/164.04; 604/174; 604/178; 604/261; 604/273; 604/115; 604/162; 604/192; 604/243; 604/263
(58) Field of Search ................................ 604/116, 117, 604/164.04, 174, 178, 261, 273, 115, 162, 243, 263, 192; 128/919, DIG. 26

(56) References Cited

U.S. PATENT DOCUMENTS

| 4,998,912 A | | 3/1991 | Scarbrough et al. |
| 5,626,829 A | * | 5/1997 | Koutrouvelis ............... 424/1.11 |
| 5,868,757 A | | 2/1999 | Koutrouvelis |
| 5,871,448 A | | 2/1999 | Ellard |
| 5,957,935 A | | 9/1999 | Brown et al. |
| 6,036,632 A | | 3/2000 | Whitmore, III et al. |
| 6,113,529 A | * | 9/2000 | Shi ................................ 600/7 |
| 6,126,904 A | * | 10/2000 | Zuellig et al. .............. 422/130 |
| 6,311,084 B1 | * | 10/2001 | Cormack et al. ........... 600/411 |
| 6,428,504 B1 | * | 8/2002 | Riaziat et al. ................ 604/65 |
| 2002/0038117 A1 | * | 3/2002 | Tokita et al. .................. 606/1 |

FOREIGN PATENT DOCUMENTS

| WO | 292 630 B1 | 3/1995 |
| WO | 98/56295 A1 | 12/1998 |
| WO | 99/37358 A1 | 7/1999 |

* cited by examiner

Primary Examiner—Gregory Huson
Assistant Examiner—Anuradha Ramana
(74) Attorney, Agent, or Firm—Scully, Scott, Murphy & Presser

(57) ABSTRACT

A needle or cylindrical element position lock includes a disposable template assembly having front and back templates halves which define an array of close-fitting through-holes to guide needles therethrough. A series of lock slides locks the positions of columns of needles positioned within the template. Each lock slide locks the position of one or more needles inserted into one or more series of the through-holes in the template, with a preferred embodiment locking two series of needles. Each lock slide has the capability of locking one or more series of needles inserted into through-holes in the needle guide template by an axial motion applied by a lock lever or cam. When the lock slide is moved axially, a locking function is provided by a wedge/clamp which engages an inserted needle. For a typical template arrangement, six lock slides are used to lock twelve columns of needles inserted into through-holes in the template assembly.

40 Claims, 5 Drawing Sheets

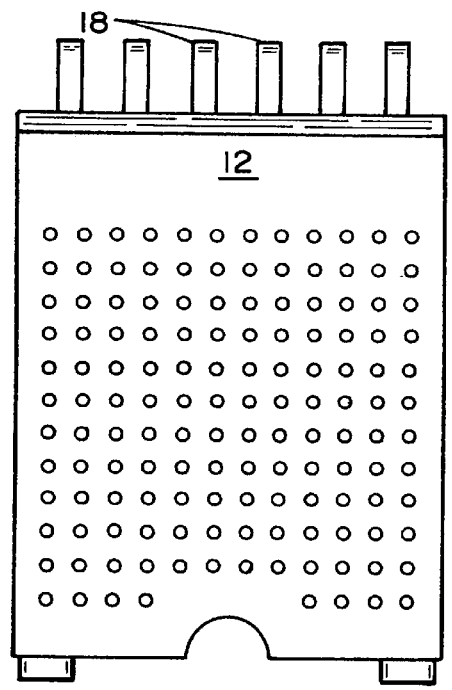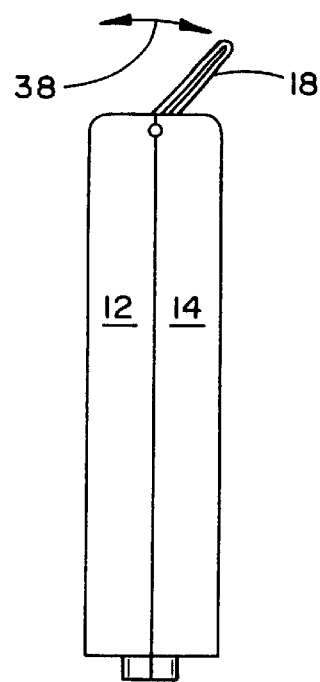
FIG. 6            FIG. 6A
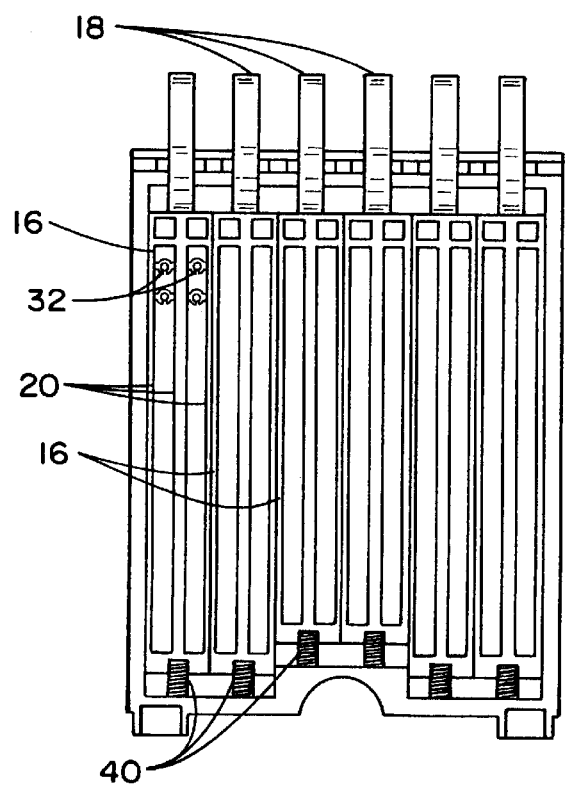
FIG. 7

NEEDLE POSITION LOCK

BACKGROUND OF THE INVENTION

1. Field of the Invention

The present invention relates generally to a position lock for locking the positions of a plurality of cylindrical elements, and more particularly pertains to a needle position lock having a provision for selectively locking and unlocking the positions of one or more needles in place to avoid inadvertent movements and positioning errors thereof.

The following discussion is specific to one embodiment of a needle position lock. Attaining and maintaining accurate needle positioning is one of the most time consuming and tedious steps in the Brachytherapy seeding procedure for placing radioactive seeds in a patient to treat prostrate cancer. Once a needle has been positioned to the correct depth, it is important that its position be accurately maintained during subsequent steps of the procedure. The needle may have an applicator or seed cartridge attached to it prior to the release of seeds. The needle may also be positioned as one of a row of needles positioned at one time. The force required to move a needle out of position is relatively low, and a needle might be accidentally moved out of position without the person releasing the seeds noticing it. In addition, the needle hubs are small and located in close proximity to one another when they are positioned in a group. This also makes it easy to inadvertently move one or more needles without detecting the positioning error. Existing needle guide templates have no provision for selectively locking and unlocking the position of each needle in place to avoid such positioning errors.

2. Discussion of the Prior Art

Current practice in the art uses a needle guide template having an ordered array of holes to guide the needles during insertion. The needle guide template uses adequately close-fitting holes, combined with an engagement depth of ten diameters or more, to effectively control angular misalignments and assure that the needles have axial (depth) movement only. However, the equipment has no provision to prevent inadvertent needle movement between initial insertion of the needle and the delivery of the radioactive seeds.

SUMMARY OF THE INVENTION

Accordingly, it is a primary object of the present invention to provide a position lock having a provision for selectively locking and unlocking the positions of one or more substantially cylindrically shaped elements such as needles in place to avoid inadvertent movements and positioning errors thereof.

Although the disclosed embodiment is for a needle position lock, the position lock is applicable to locking the position of any substantially cylindrical shaped elements such as probes and electrodes.

A more specific object of the subject invention is the provision of a needle position lock comprising a disposable template assembly having front and back templates halves which define an array of close-fitting through-holes to guide needles therethrough. The front and back template halves are held in radial alignment with each other by mating bosses to assure smooth and accurate guiding of the needles during insertion. In usage, the two halves are fastened firmly together, and preferably include snaps to allow the disposable template assembly to be inserted into a reusable or disposable mounting bracket for usage during a surgical procedure, and then detached and discarded. A series of lock slides locks the positions of columns of needles positioned within the template. Each lock slide locks the position of one or more needles inserted into one or more series of holes in the template, with a preferred embodiment locking needles in two series of holes. For a typical template arrangement, six lock slides are used to lock twelve series of needles inserted into holes in the template assembly. Additional series can be added or subtracted in increments of two or one. If desired a single column could be operated by a single lock lever.

The present invention prevents inadvertent needle movement between initial insertion of the needle and delivery of the radioactive seeds therethrough. This invention is described in terms of a needle position lock to assist a Brachytherapy seeding procedure, but could easily be adapted to lock and unlock needle positions for other minimally invasive procedures using any types of needles, or adapted to lock and unlock the positions of any substantially cylindrically shaped elements such as probes or electrodes.

The present invention comprises a needle position lock with a needle guide template which defines a hollow center between front and back halves thereof to accept needle lock slides. Each needle lock slide has the capability of locking one or more series of needles, in one or more series of holes in the template by an axial locking or unlocking movement applied by a locking lever or cam. When the lock slide is moved axially, a locking wedge/clamp collar engages with and locks each inserted needle. The needle is axially locked in position by a combination of a wedging action, due to the tapered, wedge-like profile of the hole in the wedge/clamp collar, and by a clamping action provided by flexure of the wedge/clamp collar and its attachments to supporting compression elements. Once clamped, each needle is locked to the lock slide, which is retained positioned inside the front and back template halves. This prevents the needle from moving axially until the locking lever is released and the lock slide is moved to an unlocked position. This configuration allows a column or row of needles to be easily and quickly locked in position after insertion, and then unlocked once any attachments have been. made, and the surgeon is ready to retract the needles and deliver the seeds.

In one embodiment of a typical template arrangement, a number n of lock slides could be used to lock a number of 2n holes in the template. In some embodiments a single lock slide could operate a single column of holes. Alternatively, a second series of wedge/clamp collars might be positioned inside a blank portion of the template. The second series of wedge/clamp collars might also be eliminated from the last lock slide in some embodiments.

A typical lock slide includes a main body with three compression elements attached to a beam, a beam cam surface for engagement with a cam lock lever, and a slotted cam follower pin to facilitate retraction and unlocking thereof. In a typical embodiment, two series of thirteen wedge/clamp collars each could be positioned between the compression elements, with each wedge/clamp collar being attached to each adjacent compression element by a semi-flexible member on each side thereof Each wedge/clamp collar preferably resembles a horse collar with a gap at one side. The portion of the hole inside the wedge/clamp collar and adjacent to the gap preferably provides a slip fit for the needles. The portion of the hole spaced from the gap is preferably rounded, but slightly smaller in diameter than the needle diameter. The sides of the hole between the larger and smaller portions preferably resemble a wedge with rounded ends. The semi-flexible members are preferably configured to transmit axial motions with a force required to translate the collar and wedge around the needle. Also, the semi-flexible members could flex slightly, causing the wedge/clamp collar to pinch closed, clamping down around the needle.

A cam lock lever with both external and internal cam surface provides the motion and force required to actuate the lock slide. The lock lever is rotationally mounted to the template halves, with the lever moving back and forth to move the lock slide and lock or unlock the needles. The cam locking lever has both outer and inner cam surfaces. The outer cam surface engages the beam of the lock slide, pushing it to lock. The inner cam surface engages a lock slide follower pin to pull it when the position of the lock lever is reversed. The cam surfaces and material friction properties are preferably optimized to cause the lock lever and lock slide to stay unaided in either the locked or unlocked position.

The present invention allows a surgeon to insert a needle to the desired position in the prostrate, then easily lock it in position with the simple flip of a lever. This allows the needle and seeds to remain in position after they are initially accurately positioned.

A surgeon can easily insert and position up to a whole column or row of needles in sequence, locking each one in turn. A current common practice is for an urologist to insert and position one needle at a time, and then wait for an oncologist to deliver the seeds before inserting another needle. Being able to confidently insert, position, and lock up to a whole column or row of needles in sequence, the urologist would then be free to insert a column or row of needles in another patient in an adjoining surgical suite while waiting for the oncologist to deliver the seeds. Alternatively, the oncologist could deliver seeds to another patient while waiting for the urologist. The present invention frees and enables both the urologist and oncologist to operate more independently for larger periods of time, thereby increasing productivity.

The total procedure time is reduced, since less time is lost while the urologist and oncologist trade places. In addition, less time is lost due to needles being accidentally bumped out of position, thereby causing the urologist to go back and position the needle for a second time.

Finally, instances of a needle being accidentally bumped out of position and the mislocation going undetected should be reduced, resulting in the seeds being delivered more closely to the treatment plan with more consistent results.

BRIEF DESCRIPTION OF THE DRAWINGS

The foregoing objects and advantages of the present invention for a needle position lock may be more readily understood by one skilled in the art with reference being had to the following detailed description of several preferred embodiments thereof, taken in conjunction with the accompanying drawings wherein like elements are designated by identical reference numerals throughout the several views, and in which:

FIGS. 6 and 6A are respectively front and side elevational views of the needle position lock.

FIG. 7 illustrates an alternative embodiment wherein slide springs are added to the needle position lock to bias the lock slides upwardly when the lock lever is moved to its unlock position.

DETAILED DESCRIPTION OF THE DRAWINGS

Figure 1:
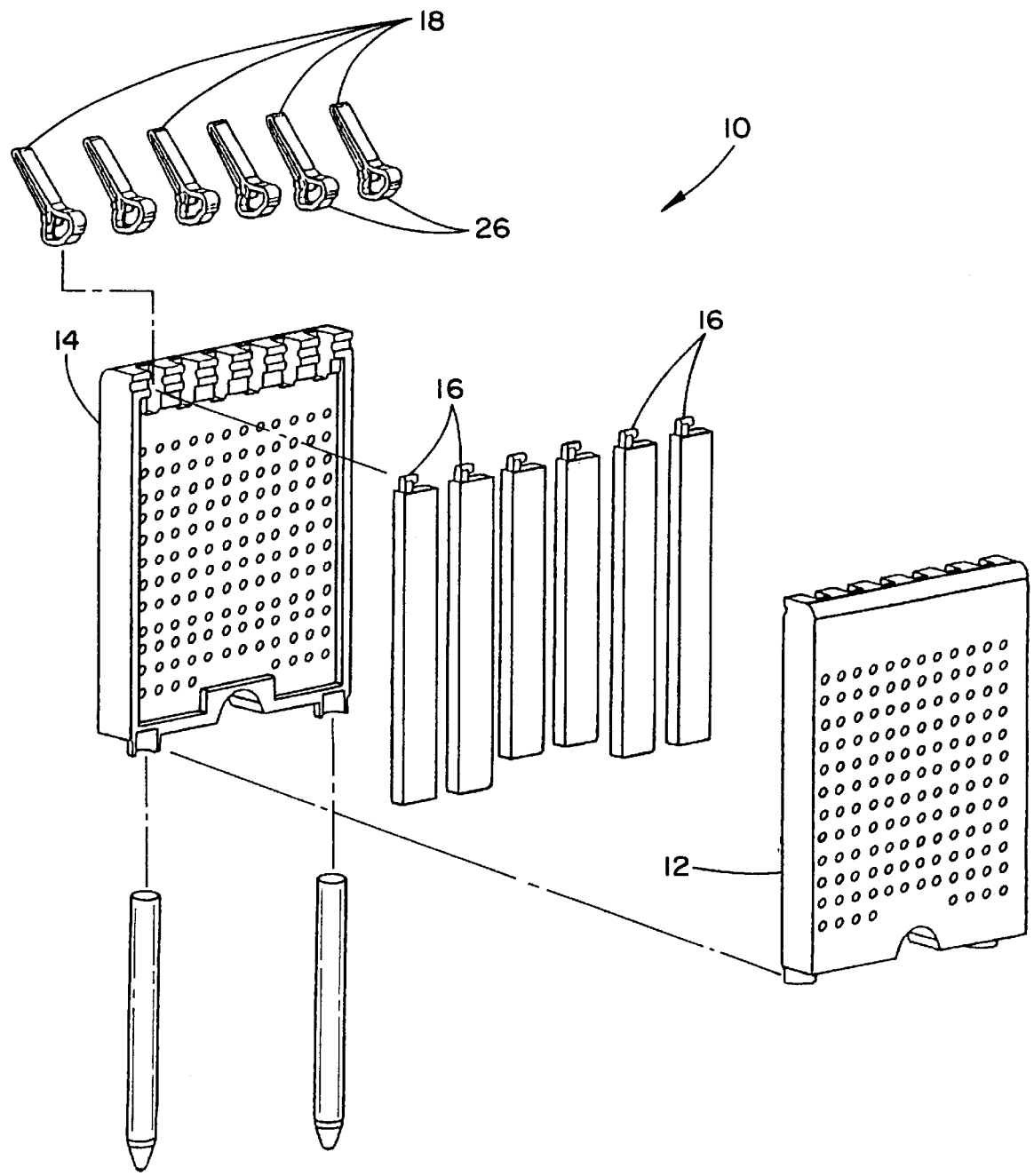
FIG. 1 is an exploded assembly view of a first embodiment of a needle position lock pursuant to the present invention.

Referring to the drawings in detail, FIG. 1 is an exploded assembly view of a first embodiment of a needle position lock 10 which is formed by a front body/template half 12 and a back body/template half 14 which form a hollow body/template which encloses a plurality of vertically slideable lock slides 16 which are vertically positionable by a plurality of cam lock levers 18 which engage the tops of the lock slides 16.

The described embodiment locks columns of needles. Other embodiments might lock rows of needles or cylindrical elements, or lock a series of needles or cylindrical elements at any angular position.

Figure 2:
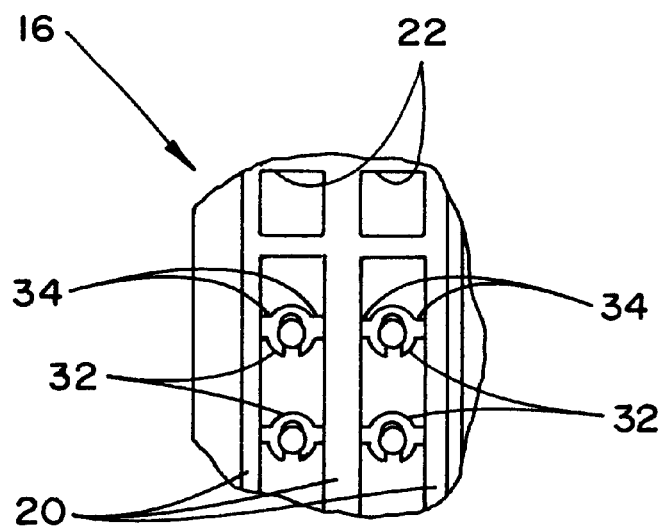
FIG. 2 is an enlarged detail view showing details of one of the vertically movable lock slides shown in FIG. 1.
Figure 3:
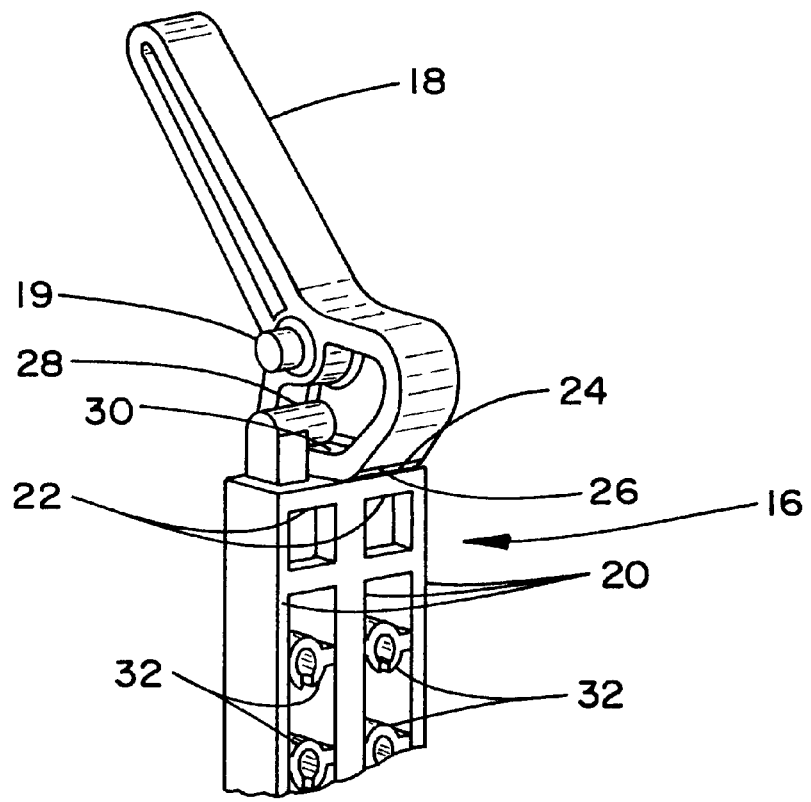
FIG. 3 is an enlarged detail view showing operational features of the cam lock lever and the lock slide.
Figure 4:
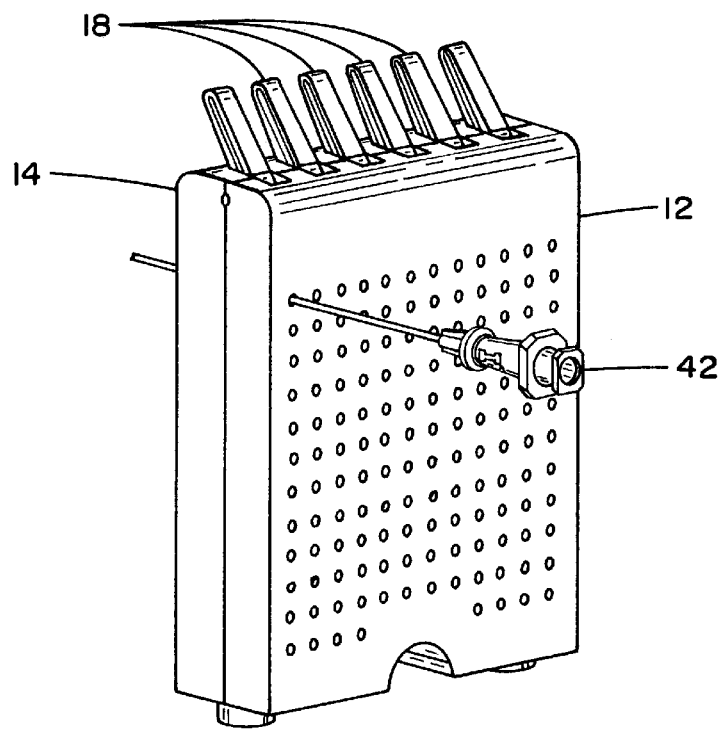
FIG. 4 shows a typical needle inserted through front and back halves of the main body of the needle position lock.
Figure 5:
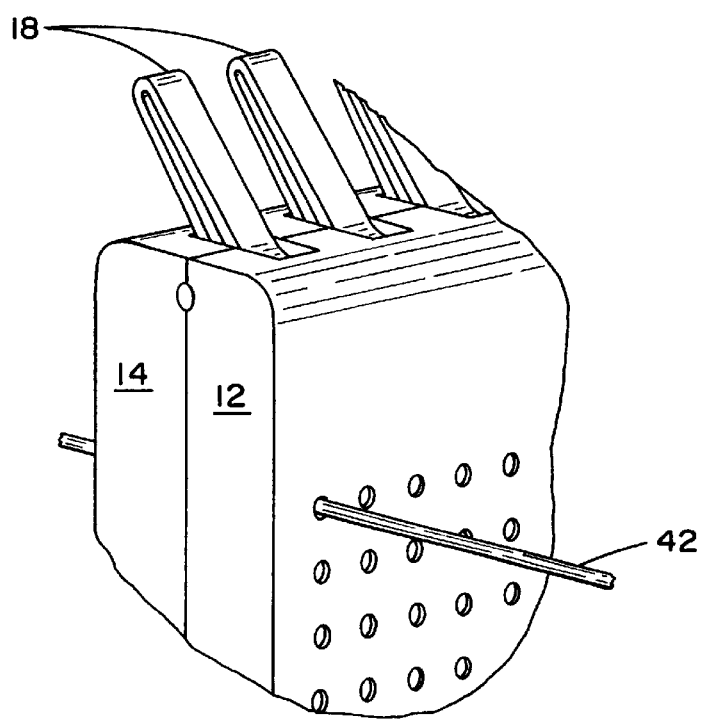
FIG. 5 is an enlarged detail view showing a needle inserted through holes in both front and back halves of the needle position lock.

FIGS. 2 and 3 are enlarged detail views of one of the vertically movable lock slides 16 shown in FIG. 1, wherein FIG. 3 also illustrates a cam lock lever 18 positioned on a top surface 24 of the lock slide 16 and under a cam follower pin 28 of the lock slide 16. Each cam lock lever 18 includes two opposed outwardly-extending mounting pins 19 which engage mounting recesses defined in the front or back body halves 12,14.

A typical lock slide 16 has a main body formed by three vertically extending compression columns 20 attached to a top beam 22 having a top cam engaging surface 24 which engages an external cam surface 26 of the cam lock 18, and a catch in the form of a slotted cam follower pin 28 which engages an internal cam surface 30 of the cam locking lever 18 to facilitate retraction and unlocking of the lock slide 16. In alternative embodiments, other types of catches, such as a defined recess, could be used to facilitate retraction of the lock slide.

Figure 8:
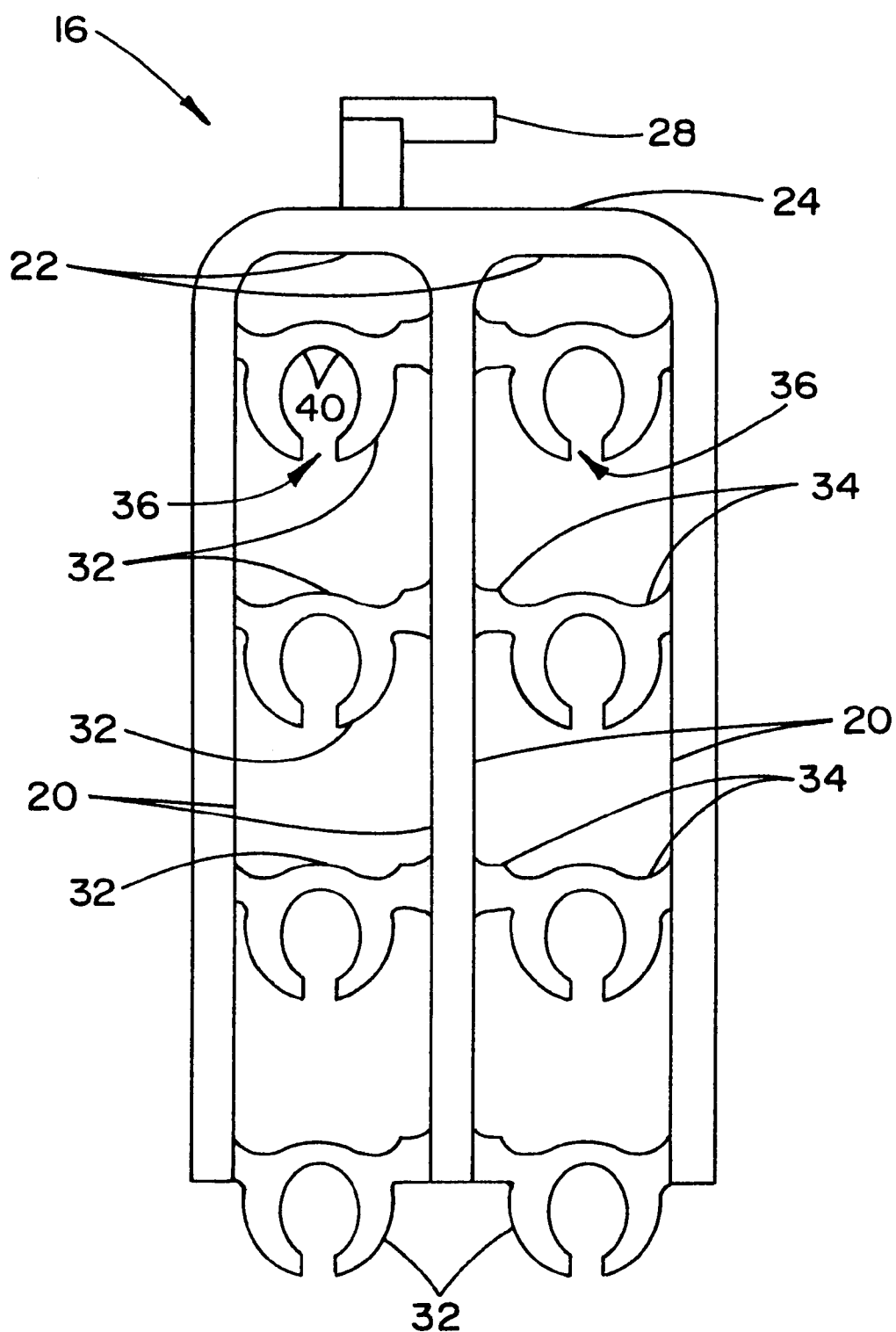
FIG. 8 is an enlarged front elevation view of one embodiment of a lock slide showing a plurality of vertically positioned columns holding a plurality of wedge/clamp collars and details of the top thereof.

Referring to FIGS. 1, 7 and 8, in one embodiment of a typical lock slide 16, two columns of twelve (12) wedge/clamp collars 32 each are positioned between two adjacent vertically-extending compression columns 20 and are attached thereto by semi-flexible members 34 on each side thereof. Referring to FIG. 8, each wedge/clamp collar 32 resembles a horse collar with a gap 36 at the bottom. The lower portion of the hole inside the wedge/clamp collar 32 provides a slip fit for needles 42. The upper portion of the hole is rounded, but is slightly smaller in diameter than the needle 42 diameter. The sides of the hole between the larger and smaller portions resemble a wedge with rounded ends. The semi-flexible side members 34 are configured to transmit the axial motion and force required to translate the collar 32 and wedge it closed over a needle 42. Also, the semi-flexible members 34 flex slightly, causing the wedge/clamp collar 32 to pinch closed, clamping down around the needle 42. A cam lock lever 18 with both an external cam surface 26 and an internal cam surface 30 preferably provides the vertical movement and force required to actuate the lock slide 16.

The cam lock lever 18 is rotationally mounted in mounting apertures provided in the front and/or back template halves 12 and 14, with the top of the lever 18 moving fore and aft as indicated by arrow 38 in FIG. 6A to move the lock slide 16 vertically and either lock or unlock the needles 42. The outer cam surface 26 engages the top surface 24 of the top beam 22 of the lock slide 10, pushing it down to a locked position. The inner cam surface 30 engages the lock slide follower pin 28 and pulls it up when the position of the locking lever 18 is reversed. The cam surfaces and material friction properties are preferably optimized to cause the lock lever 18 and lock slide 16 to stay in either a locked or an unlocked position unaided.

In an alternative embodiment illustrated in FIG. 7, slide springs 40 are added at the bottom of the lock slides 16, and bias the lock slides 16 upwardly when the lock lever 18 is moved to the unlocked position, which could eliminate the need for an inner cam surface 30 and the cam follower pin 28 in some embodiments.

While several embodiments and variations of the present invention for a position lock are described in detail herein, it should be apparent that the disclosure and teachings of the present invention will suggest many alternative designs to those skilled in the art.

What is claimed is:

1. A needle position lock having a provision for selectively locking and unlocking the position of one or more needles in place therein to avoid inadvertent needle movements and positioning errors, comprising:
    a needle guide template which defines a hollow center for movably positioning therein at least one needle lock slide, wherein the needle guide template defines an array of close-fitting through-holes to guide needles inserted therethrough;
    each lock slide locks the position of one or more needles inserted into one or more aligned series of holes in the template, and comprises one or more columns of wedge clamp collars, wherein each wedge clamp collar defines a collar hole with a gap at one end thereof, and a portion of the collar hole inside the wedge clamp collar which is closer to the gap provides a slip fit for a needle, and a portion of the hole which is further from the gap is slightly smaller than the needle diameter, such that when the lock slide is translated within the needle guide template in the direction of the gap, the slightly smaller diameter portion of the wedge clamp collar clamps around a needle.

2. The needle position lock of claim 1, wherein each lock slide locks one or more needles in two adjacent aligned series of holes in the needle guide template.

3. The needle position lock of claim 1, wherein each lock slide includes three compression members attached to a beam and extending along the aligned series of holes, with the beam having a surface for engagement with a lock lever, and a catch to facilitate retraction and unlocking of the lock slides.

4. The needle position lock of claim 3, wherein each wedge clamp collar is attached to each of two adjacent compression members by a semi-flexible member which transmits axial motion of the lock slide to cause the wedge clamp collar to clamp around a needle, and the semi-flexible members also flex slightly, causing the wedge clamp collar to pinch closed around a needle.

5. The needle position lock of claim 1, wherein each lock slide includes a lock lever which locks or unlocks the position of one or-more needles by applying an axial locking or unlocking movement to the lock slide.

6. The needle position lock of claim 5, wherein each lock lever defines both outer and inner surfaces, the outer surface pushes the lock slide to lock it, and the inner surface engages a catch on the lock slide to pull the lock slide when the position of the lock lever is reversed.

7. The needle position lock of claim 5, wherein the needle guide template comprises first and second matching and corresponding template halves, and each lock lever is rotationally mounted in the template halves, with each lock lever moving back and forth to move the lock slide to lock or unlock the needles.

8. The needle position lock of claim 1, wherein the needle position lock comprises a front template half and a back template half which form a hollow template which encloses a plurality of slideable lock slides which are positionable by a plurality of lock levers which engage the lock slides.

9. The needle position lock of claim 1, wherein the needle position lock includes at least one lock lever for applying an axial locking or unlocking movement to at least one lock slide, and at least one lock slide spring is positioned against the at least one lock slide to translate the lock slide when the lock lever is moved to its unlocked position.

10. The needle position lock of claim 1, wherein the needle guide template comprises first and second matching and corresponding template halves, and at least one lock lever is rotationally mounted in the template halves, with the lever moving back and forth to move the lock slide to lock or unlock the needles.

11. A needle position lock for selectively locking and unlocking the position of at least one needle having a diameter, said needle position lock comprising:
    a needle guide template, said needle guide template defining a hollow center and said needle guide template defining an array of through holes for receiving at least one needle therethrough; and
    at least one needle lock slide movably positioned within said hollow center, said needle lock slide defining at least one wedge clamp collar, said wedge clamp collar defining a collar hole having a gap at one end thereof and said collar hole having a first portion close to said gap and a second portion further from said gap than first portion, wherein said first portion is slightly larger than said diameter of said needle and said second portion is smaller than said diameter of said needle.

12. The needle position lock of claim 11, wherein each lock slide locks one or more needles in two adjacent aligned series of holes in the needle guide template.

13. The needle position lock of claim 11, wherein each lock slide includes three compression members attached to a beam and extending along the aligned series of holes, with the beam having a surface for engagement with a lock lever, and a catch to facilitate retraction and unlocking of the lock slides.

14. The needle position lock of claim 13, wherein each wedge clamp collar is attached to each of two adjacent compression members by a semi-flexible member which transmits axial motion of the lock slide to cause the wedge clamp collar to clamp around a needle, and the semi-flexible members also flex slightly, causing the wedge clamp collar to pinch closed around a needle.

15. The needle position lock of claim 11 wherein each lock slide includes a lock lever which locks or unlocks the position of one or more needles by applying an axial locking or unlocking movement to the lock slide.

16. The needle position lock of claim 15, wherein each lock lever defines both outer and inner surfaces, the outer surface pushes the lock slide to lock it, and the inner-surface engages a catch on the lock slide to pull the lock slide when the position of the lock lever is reversed.

17. The needle position lock of claim 15, wherein the needle guide template comprises first and second matching and corresponding template halves, and each lock lever is rotationally mounted in the template halves, with each lock lever moving back and forth to move the lock slide to lock or unlock the needles.

18. The needle position lock of claim 11, wherein the needle position lock comprises a front template half and a back template half which form a hollow template which encloses a plurality of slideable lock slides which are positionable by a plurality of lock levers which engage the lock slides.

19. The needle position lock of claim 11, wherein the needle position lock includes at least one lock lever for applying an axial locking or unlocking movement to at least one lock slide, and at least one lock slide spring is positioned against the at least one lock slide to translate the lock slide when the lock lever is moved to its unlocked position.

20. The needle position lock of claim 11, wherein the needle guide template comprises first and second matching and corresponding template halves, and at least one lock lever is rotationally mounted in the template halves, with the lever moving back and forth to move the lock slide to lock or unlock the needles.

21. A position lock for selectively locking and unlocking the position of at least one substantially cylindrically shaped element having a diameter, said position lock comprising:
    a guide template, said guide template defining a hollow center and said guide template defining an array of through holes for receiving at least one substantially cylindrically shaped element therethrough; and
    at least one lock slide movably positioned within said hollow center, said lock slide defining at least one wedge clamp collar, said wedge clamp collar defining a collar hole having a gap at one end thereof and said collar hole having a first portion close to said gap and a second portion further from said gap than said first portion, wherein said first portion is slightly larger than said diameter of said substantially cylindrically shaped element and said second portion is slightly smaller than said diameter of said substantially cylindrically shaped element.

22. The position lock of claim 21, wherein each lock slide locks one or more substantially cylindrically shaped elements in two adjacent aligned series of holes in the guide template.

23. The position lock of claim 21, wherein each lock slide includes three compression members attached to a beam and extending along the aligned series of holes, with the beam having a surface for engagement with a lock lever, and a catch to facilitate retraction and unlocking of the lock slides.

24. The position lock of claim 23, wherein each wedge clamp collar is attached to each of two adjacent compression members by a semi-flexible member which transmits axial motion of the lock slide to cause the wedge clamp collar to clamp around a substantially cylindrically shaped element, and the semi-flexible members also flex slightly, causing the wedge clamp collar to pinch closed around a substantially cylindrically shaped element.

25. The position lock of claim 21, wherein each lock slide includes a lock lever which locks or unlocks the position of one or more substantially cylindrically shaped elements by applying an axial locking or unlocking movement to the lock slide.

26. The position lock of claim 25, wherein each lock lever defines both outer and inner surfaces, the outer surface pushes the lock slide to lock it, and the inner surface engages a catch on the lock slide to pull the lock slide when the position of the lock lever is reversed.

27. The position lock of claim 25, wherein the guide template comprises first and second matching and corresponding template halves, and each lock lever is rotationally mounted in the template halves, with each lock lever moving back and forth to move the lock slide to lock or unlock the substantially cylindrically shaped elements.

28. The position lock of claim 21, wherein the position lock comprises a front template half and a back template half which form a hollow template which encloses a plurality of slideable lock slides which are positionable by a plurality of lock levers which engage the lock slides.

29. The position lock of claim 21, wherein the position lock includes at least one lock lever for applying an axial locking or unlocking movement to at least one lock slide, and at least one lock slide spring is positioned against the at least one lock slide to translate the lock slide when the lock lever is moved to its unlocked position.

30. The position lock of claim 21, wherein the guide template comprises first and second matching and corresponding template halves, and at least one lock lever is rotationally mounted in the template halves, with the lever moving back and forth to move the lock slide to lock or unlock the needles.

31. A method of selectively locking and unlocking the position of at least one needle, having a diameter, relative to a patient, comprising:
    positioning a needle guide template relative to the patient, said needle guide template defining a hollow center and an array of through holes for receiving at least one needle inserted therethrough;
    inserting at least one needle through a through hole in the needle guide template and into the patient;
    locking the at least one needle in position in the needle guide template by movably positioning at least one needle lock slide within the hollow center of the needle guide template, said needle lock slide defining at least one wedge clamp collar, said wedge clamp collar defining a collar hole having a gap at one end thereof and having a first portion close to said gap and a second portion further from said gap than said first portion, wherein said first portion is slightly larger than the diameter of said needle and said second portion is smaller than the diameter of said needle, such that when the lock slide is movably positioned within the needle guide template in the direction of the gap, the smaller diameter second portion of the wedge clamp collar clamps around a needle.

32. The method of claim 31, including locking one or more needles in two adjacent aligned series of holes in the needle guide template by movably positioning each lock slide.

33. The method of claim 32, including axially translating each lock slide along its longitudinal axis within the hollow center of the needle guide template, wherein each lock slide includes three compression members extending along the aligned series of holes.

34. The method of claim 33, wherein each wedge clamp collar is attached to each of two adjacent compression members by a semi-flexible member, and wherein axial translational movement of each lock slide causes the wedge clamp collar to clamp around a needle, flexing the semi-flexible members and pinching the wedge clamp collar closed around a needle.

35. The method of claim 31, including locking or unlocking the position of one or more needles by applying a translational locking or unlocking movement to each lock slide by a lock lever.

36. The method of claim 35, wherein each lock lever defines both outer and inner surfaces, with the outer surface pushing the lock slide to lock it, and the inner surface engaging a catch on the lock slide to pull the lock slide when the position of the lock lever is reversed.

37. The method of claim 35, wherein the needle guide template comprises first and second matching and corresponding template halves, rotationally mounting each lock lever in the template halves, and moving each lock lever back and forth to move each lock slide to lock or unlock the position of one or more needles.

38. The method of claim 31, wherein the needle position lock comprises a front template half and a back template half which form a hollow template which encloses a plurality of slideable lock slides, and movably positioning the plurality of slideable lock slides by a plurality of lock levers which engage the lock slides.

39. The method of claim 31, wherein the needle position lock includes at least one lock lever for applying an axial locking or unlocking movement to at least one lock slide, and translating the at least one lock slide by a lock slide spring when the lock lever is moved to its unlocked position.

40. The method of claim 31, wherein the needle guide template comprises first and second matching and corresponding template halves, rotationally mounting at least one lock lever in the template halves, and moving the at least one lock lever back and forth to move the lock slide to lock or unlock the at least one needle.

* * * * *